United States Patent [19]

Johnson et al.

[11] Patent Number: 5,085,086
[45] Date of Patent: Feb. 4, 1992

[54] ON-LINE LIQUID SAMPLERS

[76] Inventors: Julius T. Johnson; Robert R. Johnson, both of 416 Jacolyn Dr., NW., Cedar Rapids, Iowa 52405

[21] Appl. No.: 589,412

[22] Filed: Sep. 24, 1990

[51] Int. Cl.$^5$ .............................................. G01N 1/00
[52] U.S. Cl. .................................................. 73/863.86
[58] Field of Search ..................... 73/863.81–863.86, 73/864.33, 864.34

[56] References Cited

U.S. PATENT DOCUMENTS

| | | | |
|---|---|---|---|
| 2,865,394 | 12/1958 | Presley | 73/863.86 |
| 3,776,042 | 12/1973 | Werra et al. | 73/863.85 |
| 4,009,617 | 3/1976 | Johnson . | |
| 4,147,062 | 4/1979 | Jaeger | 73/863.83 |
| 4,580,452 | 4/1986 | Masson | 73/863.86 |
| 4,887,472 | 12/1989 | Jansen | 73/863.86 |

FOREIGN PATENT DOCUMENTS 2752284  6/1978  Fed. Rep. of Germany ... 73/863.86

Primary Examiner—Robert Raevis
Attorney, Agent, or Firm—Keil & Weinkauf

[57] ABSTRACT

An arrangement and device for on-line liquid sampling in which small samples of a liquid, particularly a sterilizable liquid, flowing through a pipe are periodically withdrawn. Sterilization of the sampling device together with a collecting container attached thereto is made possible without exposure of the device to the atmosphere as the device is mounted on the pipe. This is achieved by enveloping the sampling device with the collection container attached thereto by a flexible, high-temperature resistant enclosure such as a plastic bag, which normally seals off the liquid entry port to the device; sterilizing the device and container assembly in this condition; and providing the pressure air actuated valve in the device which serves to close the normally open valve seat to trap a sample of the liquid, with an extension which punctures the bag adjacent to the entry port incident to the actuation of the valve. The design of the device has also been improved in various respects to simplify its construction and improve its accuracy, convenience and sanitary performance in operation.

13 Claims, 2 Drawing Sheets

ON-LINE LIQUID SAMPLERS

BACKGROUND OF THE INVENTION AND PRIOR ART

The present invention relates to improvements in on-line liquid samplers and, more particularly, devices and arrangements of this kind for periodically withdrawing small samples of a liquid flowing through a pipe. A device of the kind mentioned has been disclosed in our U.S. Pat. No. 4,009,617 issued Mar. 1, 1977. The description and drawings of this older patent should be incorporated herein for purposes of disclosure.

In our earlier patent there is shown and described an instrument which is designed to collect composite samples of liquids as they are pumped through pipelines. The system uses two valves to regulate the flow of product that is sampled. The flow past the first valve which may be referred to as a check valve, lets the sample product flow into a measuring chamber which contains a flat elastomer diaphragm. When air pressure is applied to the back of this diaphragm, it directs the sample into a collection container by moving the check valve so that it closes the sampler opening to the pipeline and pops open a spring loaded self-restoring valve to allow the sample to exit from a discharge port into the collection container.

Since the two valves alternate in opening and closing, this sample design offers a high degree of sanitary protection for the pipeline being sampled. This alternating action keeps the pipeline from ever being open to the atmosphere in the plant and prevents sampled product from reentering the pipeline once it has been removed.

There are situations, however, such as when it is desired to composite-sample pipelines containing sterilized products where this design is still not sanitary enough. This is because of the problems associated with trying to mount a sampler that has been sterilized, say through autoclaving, on the pipeline without compromising the sterility of the sampler and the pipeline.

OBJECTS AND SUMMARY OF THE INVENTION

It is an object of the present invention to solve this problem with several unique improvements. More specifically, it is an object of the invention to improve the sanitary design, and also the accuracy and operating convenience of the sampling system, as well as the simplicity of construction of the device as a whole.

Briefly, one of the advantages of the arrangement according to the instant invention is that it enables the sampler and sample reception container to be sterilized, and installed on the pipeline being sampled, without compromising the sterility of either. Broadly stated, it does this by letting the user autoclave the entire sampler and container in a sealed, high temperature resistant enclosure such as a plastic bag, which prevents exposure of the sampler or collection container to the atmosphere.

An important feature in connection with this aspect of the invention consists in the new design of the first valve referred to above. In the earlier design of the sampler as disclosed in U.S. Pat. No. 4,009,617, one could autoclave the sampler and contain in a high temperature resistant plastic bag, but the sterility of the system would be compromised as soon as the bag is opened to place it on the line. According to a feature of the present invention, the first valve includes a puncturing appendage on the end, which faces the line and as a consequence, the sampling system can be sterilized in the bag and mounted on the line without opening the bag. The line can then be steam sterilized as usual with the sampler mounted on the line's sampling port, and only when pressurized air is applied to the sampler at the diaphragm measuring chamber, will the puncturing "check" valve cut through the enclosing bag and open the sampler port to the pipeline.

Preferably, in addition to the foregoing redesigned check valve, the sampler will also use an additional collar clamped onto the sampler at the point where the sampler is attached to the line. This places the plastic bag which encloses the sampler under tension over the product entry port, and facilitates the puncturing of the bag by the check valve.

Also in connection with the above-mentioned redesign of the check valve a greater amount of dish is preferably provided to the diaphragm in its normal position. Thus, when the air is applied to the back face of the diaphragm, this increased curvature allows the redesigned valve to move sufficiently to permit safe puncture of the protective plastic enclosure. In short, the space in the measuring chamber is made great enough to permit the combined movement of the diaphragm and puncturing valve to be sufficient to open the enclosing sterilization bag.

As indicated above, one wall of the flexible bag is passed through the valve housing adjacent the product-entry port thereof. The opposite wall of the bag is preferably passed through the housing adjacent the back surface of the diaphragm so that the pressure-air pulses for the actuation of the check valve act on the diaphragm through the medium of the opposite wall of the plastic bag. This enables the high temperature resistant bag to act as an additional operative barrier between the sampled product and the periodically applied activating air, the other barrier being formed by the sealingly mounted diaphragm.

Other aspects of the invention relate to the overall redesign of the housing of the sampling device. According to the invention, the housing has only two major housing portions, one for each of the two valves. More particularly, the housing portion for the first valve is horizontally mounted on the pipe, and the housing portion for the second valve extends vertically downwardly and perpendicularly from the first housing portion and has at its bottom end an outlet opening for discharging the liquid sample into the collecting container. In this fashion the overall housing configuration is confined essentially to a single plane; moreover, the new design has been rendered self-draining and thus prevents internal retention of samples between each sample pulse.

There is yet another noteworthy difference between the housing organization of the instant sampler and that of the earlier patent. The earlier instrument has an opening beyond the actual sample discharge port whereas the new design has not. The earlier design allows a small but constant atmospheric opening into the connection between the sampler and the sample container. The instant design eliminates this as a possible source of sample contamination.

Additionally the use of a small O-ring on the housing according to the invention, in combination with a discharge cap which is only partially threaded, has the effect that no threads will be exposed to product as in the earlier patent. Since threads are difficult to clean properly, this feature also creates an improvement in the sanitary design of the new sampler.

With a shorter self-restoring valve the new design of the housing has become shorter and this has the effect that the internal volume of sample carry-over is much smaller. This improves the accuracy of the sampler in critical situations such as when the volume to be sampled is quite small and has multiple product layers.

Furthermore, the new body design greatly simplifies the cleaning in place of this sampler. In the design according to our earlier patent, an attachment of tubes was necessary. In the instant design, no further attachments are required to permit cleaning solutions to pulse completely throughout the inside of the sampler. This means that a properly installed sampler will clean itself on the line—without requiring anyone to remember to prepare it for on-line cleaning as in the earlier patent.

Another object of the invention is to enable the user to employ in connection with the sampling device virtually any sample collecting container of his choosing. The housing of the sampling device has been redesigned to meet this objective. In our earlier patent the kind of bottle that could be used for collecting samples was limited by the size of the attachment head cut into the sampler body. In contrast, with the design according to the invention the user may choose virtually any bottle he wants for sample collection and he only needs to drill a hole in the bottle top which is slightly larger than the diameter of the threaded extension on the discharge cap. He then uses a cap retaining nut to secure it. When the bottle is placed on this lid, the sampler and collection container essentially become a closed system which additionally prevents the chance of external contamination of the sterile pipeline.

The discharge port is preferably of such diameter and bevel as to also allow the insertion of a plastic tube that would permit samples to be collected in evacuated sample collection bags such as a sterile plasma bag for human blood products.

BRIEF DESCRIPTION OF THE DRAWINGS

A preferred embodiment of the invention will now be described with reference to the accompanying drawings in which.

DETAILED DESCRIPTION OF THE PREFERRED EMBODIMENT

Figure 6:
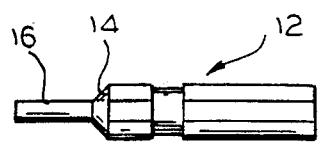
FIG. 6 is an elevational view of the check valve according to the invention, the valve being shown here separately to more clearly illustrate its design.
Figure 3:
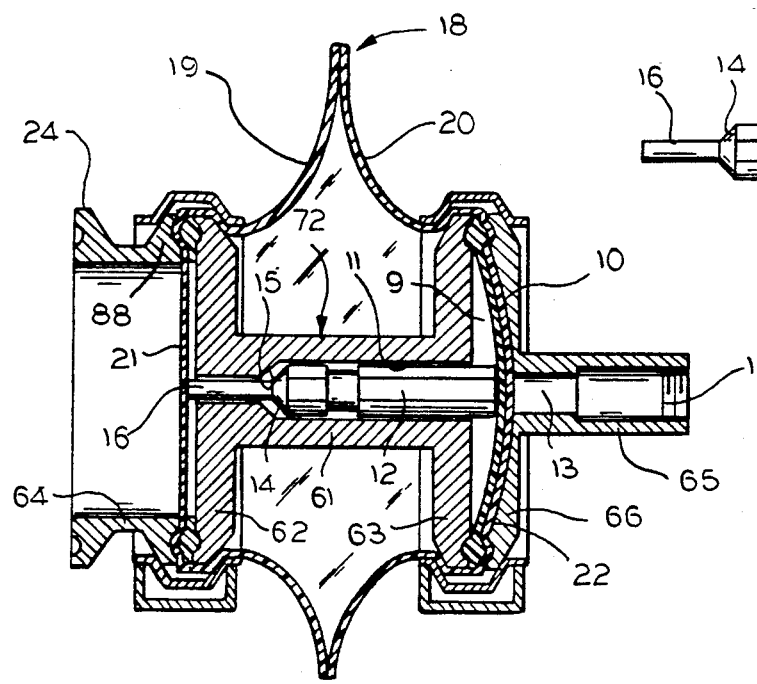
FIG. 3 is a section taken through part of the sampling device along section line 3—3 of FIG. 2.
Figure 1:
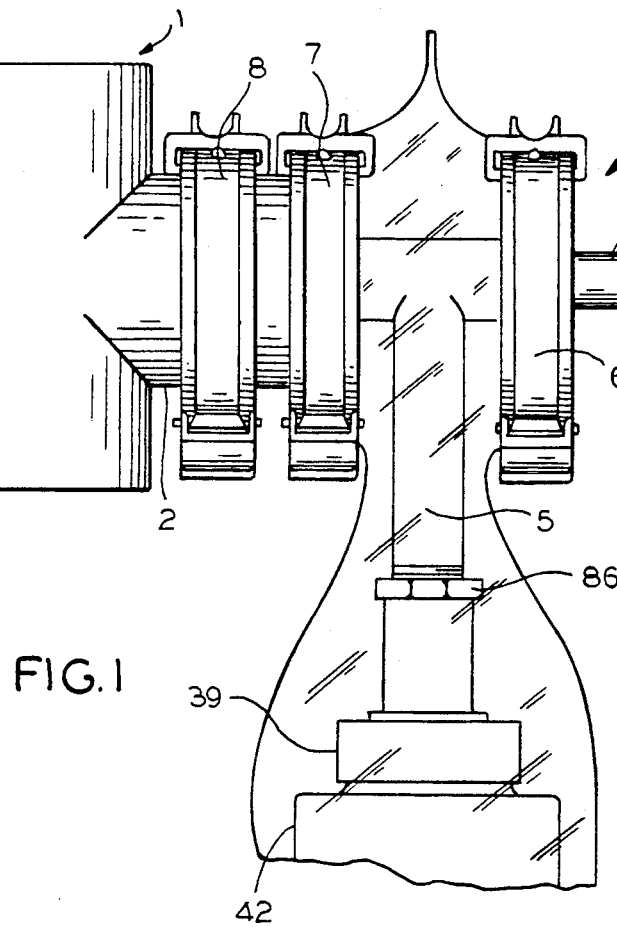
FIG. 1 is a front elevation of an arrangement according to the invention for periodically withdrawing small samples of sterilizable liquid flowing through a pipe, the figure including the sampling device, a sample collecting bottle connected thereto, and a flexible bag enclosing both the sampling device and the sample collecting bottle.
Figure 2:
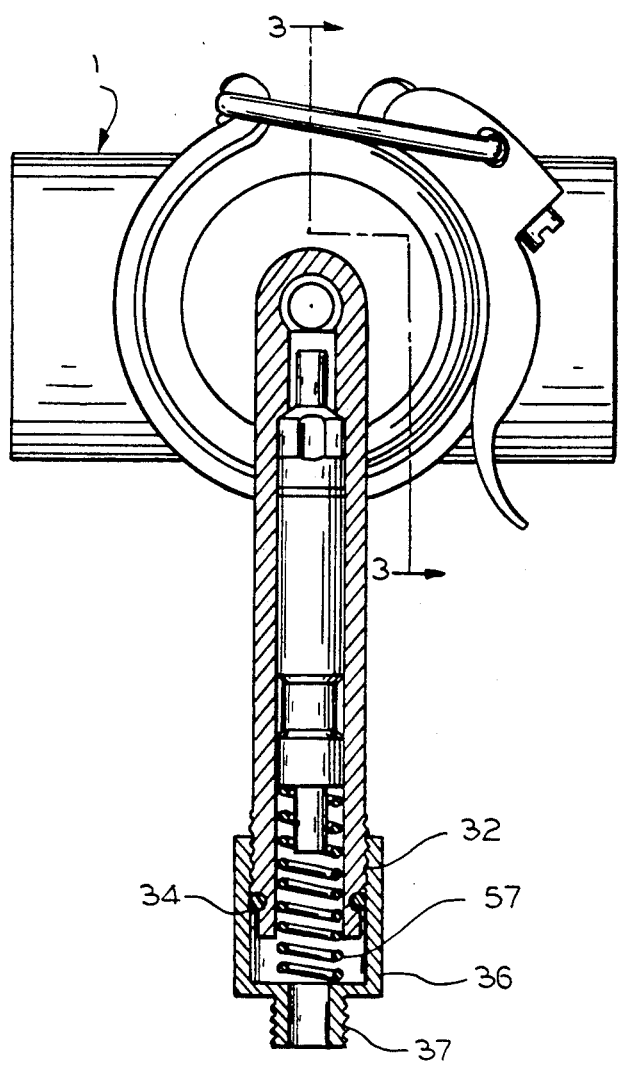
FIG. 2 is a side elevation, partly in section, of the sampling device but showing the pipe rotated by 90° with respect to FIG. 1 to indicate the flexibility with which the device can be mounted on a pipe.

Referring now to the drawings, particularly FIGS. 1 to 3, the sampling device 3 is shown mounted on the liquid-conveying pipe system by way of a T-section 1 of the pipe system. The sampling device has a generally horizontal housing portion 72 having formed therein an intake passage 11 extending axially with respect to the horizontal leg 2 of the T-section, the passage having a small entry port terminating in a valve seat 15 formed by a beveled shoulder in housing portion 72. A check valve 12 the design of which is separately shown in FIG. 6 is axially slidable in passage 11. The tapered head 14 is normally a short distance away from the valve seat 15, that is it is held in this open position by the liquid pressure in the pipe system. Near the right-hand end of passage 11 as viewed in FIG. 3, there is a diaphragm chamber 9. The flexible diaphragm 10 extends across this chamber, forming a movable wall of the chamber. The check valve 12 has a right-hand end portion projecting into the diaphragm chamber, whereby the check valve is positively moved to closed position by the pumping movement of the diaphragm. A second housing portion 5 having a discharge passage 71, FIG. 5, therein, extends vertically downwardly from the first housing portion 72, the two passages 11 and 71 being in communication with each other as visible, for example in FIG. 5. Pneumatic activating means not particularly shown in the drawings but described and illustrated in our earlier patent, U.S. Pat. No. 4,009,617 and also in U.S. Pat. No. 3,229,527, apply air pressure against the diaphragm at spaced time intervals. As a consequence, the check valve 12 with its head 14 seats against the seat 15 which is accompanied by a buildup of liquid pressure in the diaphragm chamber and intake passage 11. A spring biased self-restoring valve 51 in the discharge passage 71 momentarily opens when the pressure in the intake passage has been built up to a predetermined point.

The horizontal leg 2 of the T-section inserted in the pipe system to which the liquid to be sampled flows, at its end has a flange not particularly shown in the drawings. A flange 24 at the left end of a bag-tensioning sleeve 64 is clamped against the aforementioned flange by means of a clamp 8 of a type described in our earlier patent. Horizontal housing portion 72 consists of a tubular portion 61 and two integral disk-shaped end portions 62 and 63. The right-hand flange, FIG. 3, of tensioning sleeve 64 is clamped in the direction of disk-shaped end portion 62 by means of clamp 7. Finally, the right-hand end portion of housing 72 is clamped by a third clamp 6 against disk-shaped end portion 66 of a tubular member 65, with diaphragm 10 in this fashion being sealingly clamped between disk-shaped portions 63 and 66. Reference numeral 17 in FIG. 3 denotes the end portion of tubular member 65 to which the diaphragm activating air pressure means, not shown herein, are attached.

As will be seen from FIGS. 3 and 6, the portion of the check valve to the right of valve head 14 is cylindrical but it has two or more flat sides which allow fluid to flow into the void between the check valve and the tubular part 61 of housing portion 72. The valve stem is of cylindrical configuration but also has two or more flattened sides along which sampled liquid can flow.

The circular elastomer diaphragm 10 has a peripheral bead which is sealed in opposite grooves of the opposite faces of disk-shaped portions 63 and 66 to form a fluid-tight seal, these details being similar to those described in our earlier patent.

Figure 5:
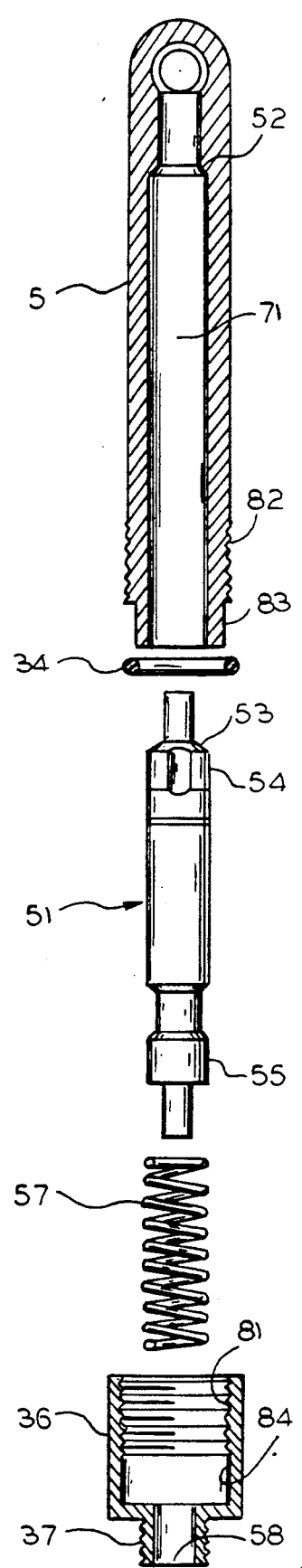
FIG. 5 is an exploded view, partly in section, of the vertically downwardly extending housing portion, together with the self-restoring valve, its bias spring and the adjustment means for this spring.

Reverting now to the self-restoring or "pop" valve which is shown in FIG. 2 and more clearly in the exploded view of FIG. 5, this valve at its upper end has a tapered valve head 53 which is normally seated, under the pressure of its bias spring 57, against the valve seat formed by the beveled shoulder 52 in the housing portion 5. Valve 51 is guided in passage 71 by guide portions 54 and 55 of relatively large diameter. Provisions, including a number of flat sides in guide portion 54, are used to insure passage of liquid along the length of the valve in its open position, these provisions being generally similar to the corresponding provisions in check valve 12, FIG. 6.

The bias of spring 51 is adjusted by a screw cap 36 which has an internal thread 81 cooperating with an external thread 82 provided near the lower end of housing portion 5.

Figure 4:
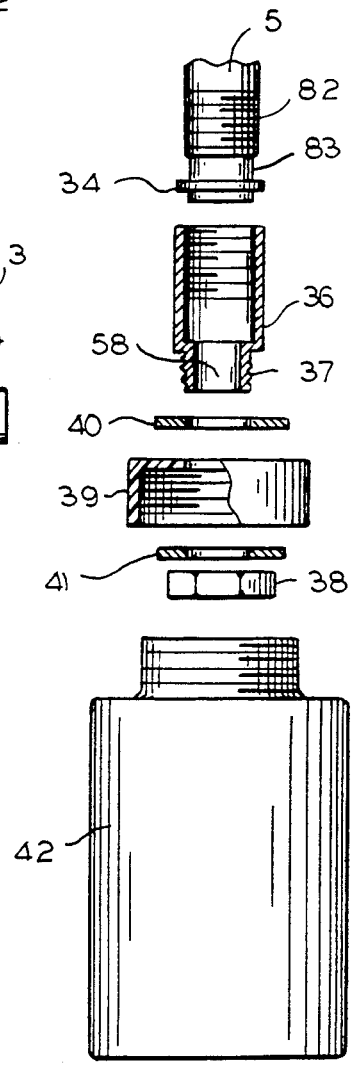
FIG. 4 is an exploded view, partly in section, of the lower portion of the vertically downwardly extending housing portion of the sampling device and also the bottle.

As will be noted from FIGS. 4 and 5, a small O-ring is provided which is slipped over the unthreaded extreme bottom section 83 of second housing portion 5 and, upon assembly of screw cap 36, is embraced by its lower, unthreaded, internal portion 84. In this manner, and in contrast to the sampler design of our earlier patent, no thread will be exposed to the sample liquid, such as for example milk. In short, the O-ring forms a physical barrier between the sample product and the adjustment threads. This is a sanitary feature which eliminates the difficulties inherent in the cleaning of threads. A threaded lock ring 86 shown in FIG. 1 serves to hold the entire screw cap assembly in place upon adjustment.

As indicated above, with the sampler design according to the invention the user may choose virtually any bottle for collection of the sample discharged by the sampler. As will be clear from FIG. 1 and the exploded view of FIG. 4 which latter shows the lower part of sampler housing portion 5 with the screw cap 36 and the means for attaching a sample-collecting bottle 42 to the end of the screw cap, all that is necessary is for the user to drill a hole into the center of the bottle cap 39 which is wide enough to fit over the extension 37 at the bottom end of the screw cap. With the bottle cap or lid 39 unscrewed from the neck of the bottle 42 the user then slips bottle cap 39 over the threaded extension 37 and then uses retainer nut 38 to fasten the bottle cap to this extension. Conventional annular washers 40 and 41 can be placed axially above and below the bottle cap, respectively, to prevent leakage and to permit the bottle cap to spin freely when the bottle 42 itself is eventually reattached to it. With the bottle thus placed on its cap, the sampler and the collection container essentially become a closed system which prevents external contamination of a sterile pipeline.

Collecting samples in a bag requires a special type of bag with a tube attached to it, such as the bags used in hospitals to collect blood and plasma for transfusion. The outlet opening 58 on the sampler can be cut to an appropriate diameter so that the end of the tube on these special bags can be tightly inserted into the sampler's outlet opening.

As mentioned above, one aspect of the invention is an arrangement, particularly for use with pipe systems carrying a sterilizable liquid, which makes it possible for the user to autoclave the entire sampler and collection container assembly in a sealed, high-temperature resistant enclosure, such as a flexible plastic bag, which prevents exposure of the sampler or collection container to the atmosphere as soon as the bag is opened to place it on the line. The embodiment of the invention shown herein, especially in FIGS. 1, 3 and 6, incorporates this highly advantageous arrangement. As will be seen from these figures, the envelope is in the form of a flexible high-temperature resistant bag 18 consisting of two halves 19, 20 which, after they have been placed on the device 3 and the attached container 42 in the manner illustrated, are adhesively or otherwise sealed together as indicated. Each of the two halves of the bag is fully intact, that is forms an unbroken sheet. More particularly, the left half of the bag, designated 19, is placed on the assembly of the sampler along the outside of the disk-shaped end portion 62 of the sampler housing so as to cover the small liquid entry port into the housing portion 72, and it is held there by the clamp 7 as shown. On the other hand, the right-hand half 20 of the bag is placed directly along the outside of diaphragm 10, and it is held in place together with the diaphragm, by means of clamp 6. As a result, after the two halves of the bag have been joined together, as mentioned above, the sampler and the collection container attached thereto, can be safely autoclaved without affecting the integrity of the system.

In this condition, of course, the sampler would be inoperative due to the entry port being covered by the left half 19 of the bag. In order to make proper operation of the sampler possible notwithstanding the sampler and container assembly being hermetically sealed in this normal condition, the check valve, according to a significant feature of the invention, is designed so as to puncture the bag—the left half 19 thereof—in response to pressure air pulses, more particularly the first of these pulses, being applied to the outside of diaphragm 10. To this end check valve 12, FIGS. 3 and 6, is provided with a bag-puncturing extension 16 at its left end. After the bag has thus been punctured, the entry port of the sampler is open to the pipeline.

It will be appreciated, of course, that, with the right half 20 of plastic bag 18 extending along the outside of diaphragm 10, the pressure air pulses are being applied to the outside of the diaphragm through the medium of the corresponding portion of the bag.

In connection with the foregoing feature, provisions have been made to tension the portion of the bag passing along the entry port, thereby to insure the proper puncturing of the bag by check valve extension 16. These provisions are in the form of tensioning sleeve 64 which is axially interposed between horizontal leg portion 2 of the T-section 1 and disk-shaped portion 62 of the sampler housing, along the outside of which the left half 19 of the bag passes. Tensioning sleeve 64 has a flange at each end, namely a flange 88 at the right end which bears against disk portion 62 through the medium of bag half 19, and, at the left end, flange 24 which is surrounded by third clamp 8. All three clamps are of the quick-release type and are of similar, well-known construction.

In mounting the sampler on the T-section the sampler assembly including tensioning sleeve 64 is pushed against the end of horizontal leg 2 to clamp the bag down and clamps 7 and 8 are tightened to hold the entire assembly in place in this condition.

Likewise, in connection with the modification of the check valve to include puncturing extension 16, diaphragm 10 is given a greater amount of dish in its normal position, and the diaphragm chamber 9 is correspondingly configured. Due to the greater curvature of diaphragm 10 as compared with the construction according to our earlier patent, when the pressure air is applied in the direction of the right side of the diaphragm, check valve 12 is moved to the left by an amount sufficient to insure safe puncture of bag 18 and subsequently the closing of the valve seat.

Briefly, the sampling operation of the device is as follows: When the diaphragm is moved inwardly into the sampling chamber by air pressure against its outer surface, the pressure created by the movement of the diaphragm causes the puncturing of the bag by extension 16 of the check valve and then forces the check valve to shift to a position where it blocks communication through the entry port between intake or sampling passage 11 and the liquid conduit or line and thereby traps the liquid present in the intake passage. The pressure also activates the self-restoring or pop valve 51 to move it to a non-blocking relationship between intake passage 11 and discharge passage 71, that is it moves head 53 of the pop valve away from its seat 52. This in turn allows the topped liquid to flow out of the intake passage into the discharge passage from which it is collected.

When the air pressure on the outer side of the diaphragm is released, the latter returns to normal position. When the pressure in the intake passage 11 due to the liquid discharge drops to a value at which the liquid pressure force drops below the bias force of spring 57 of the pop valve, the pop valve moves back to blocking relationship between intake passage 11 and discharge passage 71. The pressure in the main line moves the check valve into non-blocking position between the liquid entry port and intake passage 11 and the sampling chamber again fills with liquid entering it through the small entry port.

Upon initiation of the second pressure pulse, the diaphragm 10 moves from its curved shape as shown in FIG. 3 under the increasing pressure between the pneumatic side of the diaphragm and the face of disk-shaped portion 63. As the diaphragm moves toward the left, the check valve is again moved positively by the diaphragm until it is seated on the valve seat 15. In so moving the check valve 12, the diaphragm causes pressure to be built up in the intake passage. When the check valve reaches its closed position, the liquid pressure in the intake passage builds up sufficiently to cause the pop valve to open. Liquid then flows again past the discharge port formed by valve head 54 no longer seated on seat 52, and thence out of the sampler at outlet opening 58. The volume of each sample portion per pulse corresponds substantially to the volume displaced by the diaphragm's movement in the diaphragm chamber.

The most common practice for cleaning lines in liquid processing plants is known as "cleaning-in-place" or "C.I.P.". When this is done, hot washing solutions are pumped through the lines and it is very desirable for any attachments to the line, such as the instant sampler, to also be able to be cleaned on the line without removing or otherwise disassembling them.

The sampler according to the invention is designed to be internally washed through its normal air operated pulsing action when the cleaning solutions are pumped through the lines. Just as in the case of sampling products, the hot cleaning solutions are being "sampled", exposing the internal sampler valves, spring, diaphragm and other surfaces to the cleaning process.

It will be noted that the sampler according to the invention is of a much simpler overall configuration than that of our earlier patent: While the latter has three distinct housing portions each extending in a direction perpendicular to the other two, the device according to the invention has only two housing portions which share a common plane. Moreover, due to the fact that the second housing portion extends vertically downwardly from the first, horizontal housing portion the instant sampler is self-draining and, as mentioned above, it permits cleaning in place without any additional attachments.

The body of the instant sampler also permits more accurate samples to be collected due to the reduction of the sample volume carried over between sampling impulses. This is a combined result of the smaller body, a shortened self-restoring valve and the self-draining feature just referred to.

It is believed that the invention and its various attendant advantages will be fully understood from the foregoing description, and it is clear that numerous changes may be made in the form, construction and arrangement of the several parts without departing from the spirit or scope of the invention, or sacrificing any of its attendant advantages, the forms herein disclosed being preferred embodiments for the purpose of illustrating the invention.

What is claimed is:

1. An arrangement, including a sampling device and a sample-collecting means attachable thereto, for periodically withdrawing small samples of sterilizable liquid flowing through a pipe, said device comprising
    a housing,
    means for mounting said housing on said pipe,
    means for attaching said sample-collecting means to said device,
    a valve movably disposed in said housing,
    a normally open liquid intake port provided in said housing near the point where said housing is mounted on said pipe,
    a normally closed sample discharge port in said housing, said valve being arranged to be periodically operated to close said intake port and thus trap a sample of the liquid in said housing,
    means responsive to the pressure of said liquid sample to momentarily open said discharge port and thus permit said sample to flow into said collecting means,
    said housing together with said collecting means being completely enveloped by a flexible high-temperature resistant enclosure one wall of which normally seals off said intake port, and
    said valve having adjacent said intake port an extension designed, incident to its operation, to puncture said enclosure,
    whereby sterilization of the sampling device together with the collecting means attached thereto is made possible without exposure of said device to the atmosphere before said device is mounted on said pipe.

2. An arrangement as claimed in claim 1, wherein said means for mounting said housing on said pipe include means for tensioning said enclosure wall adjacent said intake port so as to facilitate the puncturing of said wall by said valve extension.

3. An arrangement as claimed in claim 1,
wherein said housing has a diaphragm chamber and a diaphragm therein arranged to be periodically displaced in said chamber by pressure-air pulses applied to the side of said diaphragm opposite said chamber to periodically move said valve, and
wherein the other wall of said flexible enclosure is passed along said opposite side of said diaphragm.

4. An arrangement as claimed in claim 3, wherein said diaphragm has an amount of dishing sufficient to impart to said valve a stroke long enough to insure safe puncturing of said enclosure by the valve.

5. An arrangement as claimed in claim 1, wherein said enclosure is in the form of a flexible plastic bag consisting of two halves, said halves being jointed together after having been passed through opposite ends of said housing.

6. An arrangement as claimed in claim 1, wherein said means for momentarily opening said discharge port are in the form of another valve which is spring loaded and hence self-restoring such that the two valves are operated in alternating sequence.

7. An arrangement as claimed in claim 6, wherein said housing includes two interconnected portions, one of said portions housing said first-mentioned valve and the other portion housing said self-restoring valve.

8. An arrangement as claimed in claim 7, wherein the second housing portion vertically depends from said first housing portion and includes said self-restoring valve, its loading spring and, at the end of said second housing portion, an outlet opening and said means for attaching said sample-collecting means to said device.

9. An arrangement as claimed in claim 8, wherein at the end of said second housing portion there is provided a screw cap for adjusting the compression of the loading spring, said cap having an end wall with said outlet opening therein through which the liquid sample emerges from said second housing portion.

10. An arrangement as claimed in claim 9, wherein the a bottom end of said second housing portion has an outer thread cooperating with corresponding inner thread of said screw cap,
wherein the last-mentioned outer and inner threads are of only limited extent, and
wherein an O-ring is provided between the lower, unthreaded portions of said screw cap and said second housing portion, whereby said threads are kept from being exposed to sampled liquid and corresponding difficulties in the cleaning of the sampling device are eliminated.

11. An arrangement as claimed in claim 8 wherein the means for attaching said sample-collecting means to said device consist of a screw cap having an externally threaded extension, engageable by a retention nut for securing the top portion of a collecting means thereto.

12. A sampling device for periodically withdrawing small samples of a liquid flowing through a pipe, said device comprising
two alternately acting valves each movably disposed in a respective tubular housing,
the first valve housing having means for mounting said housing horizontally on said pipe, and having a normally open intake port to admit liquid from said pipe, and the second valve housing having a normally closed discharge port for admitting liquid sampled by said first valve into said second valve housing, and said second valve being spring loaded and hence self-restoring,
said first valve housing also having a diaphragm chamber with a diaphragm therein arranged to be periodically displaced in said chamber by pressure-air pulses applied to the side of said diaphragm opposite said chamber to move said first valve to close said intake port and to force the liquid sample thus trapped through said discharge port into said second valve housing,
the second housing extending vertically downwardly from said first housing in perpendicular relationship thereto, and near its bottom end having an outlet opening for discharging the liquid sample into a sample-collecting means,
said second housing having a bottom section in which said outlet opening is formed, said bottom section having an external thread engageable by a retention nut for mounting the top portion of said collecting means, such as a lid detached from a collecting bottle thereto, and
the bottom section having said external thread being in the form of a screw cap arranged to surround the bottom end of said second housing, said screw cap serving for the adjustment of the compression force of the loading spring for said self-restoring valve.

13. A device as claimed in claim 12, wherein said screw cap has an inner thread of limited extent,
wherein the bottom end of said second valve housing has a cooperating outer thread of limiting extent, and
wherein an O-ring is provided between the lower unthreaded portion of the inside of said screw cap and the lower unthreaded portion of the outside of the bottom end of said second valve housing,
whereby said cooperating threads are kept from being exposed to sampled liquid and hence corresponding difficulties in the cleaning of the sampling device are eliminated.

* * * * *

UNITED STATES PATENT AND TRADEMARK OFFICE
CERTIFICATE OF CORRECTION

PATENT NO.   : 5,085,086
DATED        : Feb. 4, 1992
INVENTOR(S)  : Johnson et al.

It is certified that error appears in the above-identified patent and that said Letters Patent is hereby corrected as shown below:

Claim 13,
  Column 10, Line 44:

That part reading "thread of limiting extent" should read
       -- thread of limited extent --

Signed and Sealed this

Eighteenth Day of May, 1993

Attest:

MICHAEL K. KIRK

*Attesting Officer*     Acting Commissioner of Patents and Trademarks